United States Patent [19]

Paasch et al.

[11] Patent Number: 5,145,603
[45] Date of Patent: Sep. 8, 1992

[54] FREE-FLOWING, NONIONIC FAT DISPERSION

[75] Inventors: Stefan Paasch, Wolfenbuettel; Holger Tesmann, Duesseldorf; Rolf Kawa, Monheim, all of Fed. Rep. of Germany

[73] Assignee: Henkel Kommanditgesellschaft auf Aktien, Duesseldorf-Holthausen, Fed. Rep. of Germany

[21] Appl. No.: 720,811
[22] PCT Filed: Jan. 4, 1990
[86] PCT No.: PCT/EP90/00013
§ 371 Date: Jul. 11, 1991
§ 102(e) Date: Jul. 11, 1991
[87] PCT Pub. No.: WO90/07976
PCT Pub. Date: Jul. 26, 1990

[30] Foreign Application Priority Data

Jan. 12, 1989 [DE] Fed. Rep. of Germany ....... 3900701

[51] Int. Cl.$^5$ .................. B01F 17/42; A61K 7/00; A61K 9/10
[52] U.S. Cl. ................... 252/311; 252/308; 252/315.1; 252/351; 424/59; 524/539; 106/271
[58] Field of Search ............ 252/308, 311, 315.1, 252/351; 424/59; 524/539; 106/271

[56] References Cited

U.S. PATENT DOCUMENTS

| | | | |
|---|---|---|---|
| 3,993,580 | 11/1976 | Galusky | 252/311 |
| 4,446,165 | 5/1984 | Roberts | 426/602 |
| 4,536,324 | 8/1985 | Fujiwara et al. | 252/311 |
| 4,670,185 | 6/1987 | Fujiwara et al. | 252/311 |
| 4,832,858 | 5/1989 | Vishnupad et al. | 252/49.5 |
| 4,959,206 | 9/1990 | Noguera et al. | 424/70 |
| 5,015,469 | 5/1991 | Yoneyama et al. | 424/59 |
| 5,025,061 | 6/1991 | Ishidoya et al. | 524/539 |

Primary Examiner—Richard D. Lovering
Assistant Examiner—N. Bhat
Attorney, Agent, or Firm—Ernest G. Szoke; Wayne C. Jaeschke; Norvell E. Wisdom, Jr.

[57] ABSTRACT

Free flowing aqueous dispersions of non water soluble paraffin hydrocarbons and fats that melt at 30° to 100° C., the dispersions containing up to 60 weight percent of these substances, are produced by using as dispersant up to 1 weight percent of non-ionic surface active ethylene oxide addition products with an HLB value between 12 and 19.6. Preferred dispersions contain 30 to 50 weight percent of fatty alcohols, and, as a dispersant, the products of addition of 20 to 100 moles of ethylene oxide to a fatty alcohol with 16 to 22 carbon atoms, the amount of dispersant being 0.1 to 0.5 weight percent relative to the whole dispersion.

16 Claims, No Drawings

FREE-FLOWING, NONIONIC FAT DISPERSION

BACKGROUND OF THE INVENTION

1. Field of the Invention

This invention relates to an aqueous dispersion of a meltable fat which is flowable and pumpable at normal temperature and which contains a large quantity of up to 60% by weight of the fat and a relatively small quantity of up to 1% by weight of a nonionic emulsifier.

2. Statement of Related Art

Fats are used for the production of numerous liquid, aqueous and emulsion-form preparations for cosmetic, pharmaceutical or industrial purposes, influencing the properties of these preparations in dispersed form. The incorporation of fats, which are wax-like substances solid at normal temperature, requires melting and uniform stable dispersion in a similarly heated solution or emulsion of the other components. This procedure involves considerable effort, so that it would be of advantage for many users if the fats in question were already available in the form of a stable dispersion concentrate which could be homogeneously dispersed in other aqueous preparations simply by mixing.

Pumpable dispersions of fatty alcohols containing 10 to 25% by weight linear $C_{14-22}$ fatty alcohols and 0.01 to 1.0% by weight of a cationic emulsifier were already known from EP 282 864 A 1.

However, cationic dispersions of this type are relatively unsuitable for use in aqueous media containing anionic surfactants or polymers because they cause separations. In addition, it appeared desirable stably to disperse more than 25% by weight of the solid to enable dispersions of the type in question to be transported and stored at relatively reasonable cost.

DESCRIPTION OF THE INVENTION

It has now been found that meltable fats can be converted into low-viscosity dispersions of relatively high solids concentration using very small quantities of certain nonionic emulsifiers.

SUMMARY OF THE INVENTION

The present invention relates to aqueous dispersions—flowable at 20° C.—of water-insoluble fats meltable at a temperature in the range from 30° to 100° C., characterized by a content of:

(A) 25 to 60% by weight of one or more fats (B) 0.1 to 1% by weight of one or more nonionic surface-active ethylene oxide adducts having an HLB value above 10 as emulsifier and (C) 39 to 74.9% by weight water.

DESCRIPTION OF PREFERRED EMBODIMENTS

Suitable fats (A) are paraffin hydrocarbons and any water-insoluble fat derivatives melting at temperatures in the range from about 30° to 100° C. which do not form mixed phases with water at temperatures in that range and, more particularly, do not form liquid crystalline phases or gels at temperatures in that range. Examples of suitable fats are, above all, $C_{14-22}$ fatty alcohols or mixtures thereof. $C_{12-22}$ fatty acids or mixtures thereof, fatty acid/fatty alcohol esters of $C_{12-22}$ fatty acids and fatty alcohols, $C_{16-44}$ dialkyl ethers, ethylene glycol or propylene glycol difatty acid esters or fatty acid triglycerides of $C_{12-18}$ fatty acids and mixtures of these fats.

Particularly suitable emulsifiers (B) are nonionic adducts of ethylene oxide with fatty alcohols, fatty acids, fatty amides, fatty acid alkanolamides, fatty acid monoglycerides, fatty acid propylene glycol monoesters, fatty acid sorbitan partial esters or with other fatty acid polyol partial esters, with alkyl monoglycosides or oligoglycosides, with methyl glucoside monofatty acid esters and with alkylphenols. The emulsifiers mentioned should contain a $C_{12-22}$ alkyl or acyl group. The ratio by weight of hydrophilic to lipophilic groups in these ethylene oxide adducts should be such that the weight of the hydrophilic polyethylene glycol ether groups formed by ethylene oxide and the polyol ether groups should make up about 60 to 96% by weight of the molecule as a whole. In these ethylene oxide adducts which are suitable for the preparation of the fat dispersions according to the invention, the HLB value according to the equation $HLB = (E+P)/5$ (where E is the content of oxyethylene groups in % by weight and P is the content of polyolether groups in % by weight in the adduct) is thus of the order of $60-96/5 = 12-19.2$.

The production of ethylene oxide adducts of this type by addition of ethylene oxide onto compounds containing labile hydrogen atoms, for example onto compounds containing hydroxyl groups, carboxyl groups or amino groups, is known (cf. H. Schönfeldt, *Surface Active Ethylene Oxide Adducts*, Pergamon Press 1969). It is also known that mixtures of homologous polyglycol ethers, of which the average degree of ethoxylation corresponds to the molar quantity of ethylene oxide added on, rather than individual polyglycol ethers are formed in this way.

Particularly suitable ethylene oxide adducts are the adducts of 20 to 100 moles ethylene oxide with $C_{12-22}$ fatty alcohols, with $C_{12-22}$ fatty acids, with fatty acid monoglycerides, with fatty acid sorbitan monoesters or with fatty acid propylene glycol monoesters of $C_{12-22}$ fatty acids, with castor oil or hydrogenated castor oil, with an alkyl monoglycoside or oligoglycoside containing 12 to 22 carbon atoms in the alkyl group or with an alkylphenol containing 8 to 15 carbon atoms in the alkyl group and mixtures of these emulsifiers.

The dispersions according to the invention become particularly thin-flowing if the emulsifier is present in low concentrations of only 0.1 to 0.5% by weight of the dispersion as a whole. The emulsifier components (B) to be used in accordance with the invention are preferably the only surface-active substances used in the dispersions according to the invention. The additional presence of ionic surfactants is not only generally of no use, it can occasionally have an adverse effect on flowability. However, it can be entirely favorable to the stability of the dispersions to add relatively small quantities, for example about 0.1 to 3% by weight, of water-soluble polymers. Preferred water-soluble polymers are nonionic polymers, such as for example hydroxyethyl cellulose, methyl hydroxypropyl cellulose, polyvinyl pyrrolidone, polyvinyl alcohol, polyethylene oxides, nonionic starch ethers, xanthan gum, guar and vegetable gums. However, ionic polymers, for example anionic polyacrylates and polyacrylic acid copolymers, carboxymethyl cellulose, carboxyethyl starch or maleic acid copolymers, or cationic polymers, may also be added to the dispersions according to the invention without causing any troublesome reactions.

One particularly preferred embodiment of the invention is a dispersion containing a $C_{14-22}$ fatty alcohol in a quantity of 30 to 50% by weight as the fat and an adduct of 20 to 100 moles ethylene oxide with 1 mole of a $C_{16-22}$ fatty alcohol in a quantity of 0.1 to 0.5% by weight, based on the dispersion as a whole, as the emulsifier.

The dispersions according to the invention are prepared in the usual way by heating the fat and the emulsifier together beyond the melting point of the mixture with intensive mixing. The water heated to substantially the same temperature is then added with stirring or in standard mixing and emulsifying units. An oil-in-water emulsion is formed. The final emulsion may then be cooled to a temperature below the melting point of the fats. The emulsified fats solidify and a stable dispersion is formed.

The dispersions obtained by the process according to the invention may readily be further diluted with water at normal temperature (20° C.) and may be adjusted to any relatively low concentrations of the fat. They may also readily be added to other aqueous preparations, irrespective of their ionicity, and disperse spontaneously therein without any instability or separation occurring. Accordingly, they are suitable for the storage, transport and processing of meltable fats in a water-dilutable form flowable at normal temperature.

The following Examples are intended to illustrate the invention without limiting it in any way.

EXAMPLES

1. Preparation of dispersions according to the invention
   1.1 Fats used
   CSAL (cetyl/stearyl alcohol, ratio by weight 50:50)
   CP (cetyl palmitate)
   EGS (ethylene glycol distearate)
   SAC (stearic acid)
   1.2 Emulsifiers used
   TA 20 (adduct of 20 moles ethylene oxide with cetyl/stearyl alcohol, ratio by weight 30:70)
   TA 80 (adduct of 80 moles ethylene oxide with cetyl/stearyl alcohol, ratio by weight 30:70)
   NP 50 (adduct of 50 moles ethylene with nonylphenol)
   HRE 60 (adduct of 60 moles ethylene oxide with hydrogenated castor oil (12-hydroxystearic acid triglyceride)
   GMS 24 (adduct of 24 moles ethylene oxide with glycerol monostearate)
   1.3 Preparation of the dispersions The fat and emulsifier were heated and mixed at a temperature above the melting point of the mixture, in the present case at 80° C. The mixture was then mixed while stirring with the water which had also been heated to 80° C. Spontaneous emulsification occurred. The emulsions obtained were then rapidly cooled to +20° C.

The composition and viscosity of the emulsions is shown in the following Table. Viscosity was measured at +20° C. 5 hours after preparation of the emulsion using a rotational viscosimeter at a shear rate of 400 s$^{-1}$.

TABLE

| Composition | 1 | 2 | 3 | 4 | 5 | 6 | 7 | 8 | 9 | 10 | 11 | 12 |
|---|---|---|---|---|---|---|---|---|---|---|---|---|
| CSAL | 40 | 40 | 40 | 40 | 60 | 40 | 40 | 40 | — | — | — | — |
| CP | — | — | — | — | — | — | — | — | 40 | 40 | — | — |
| EGS | — | — | — | — | — | — | — | — | — | — | 40 | — |
| SAC | — | — | — | — | — | — | — | — | — | — | — | 40 |
| TA 20 | 0.1 | 0.25 | 0.5 | 0.75 | 0.15 | — | — | — | 0.25 | 2.0 | 0.2 | — |
| TA 80 | — | — | — | — | — | — | — | — | — | — | — | 1.0 |
| NP 50 | — | — | — | — | — | 1 | — | — | — | — | — | — |
| HRE 60 | — | — | — | — | — | — | 0.5 | — | — | — | — | — |
| GMS 24 | — | — | — | — | — | — | — | 0.25 | — | — | — | — |
| Water | 59.9 | 59.75 | 59.5 | 59.25 | 39.85 | 59 | 59.5 | 59.75 | 59.75 | 58 | 59.8 | 59 |
| Viscosity 20° C. [Pa s] | 0.2 | 0.3 | 0.5 | 1.5 | 0.85 | 0.21 | 0.2 | 0.17 | 0.25 | >1 | 0.02 | 0.16 |

What is claimed is:

1. An aqueous dispersion, comprising:
   (A) 25 to 60% by weight of material selected from the group consisting of water-insoluble fats which melt at a temperature in the range from 30° to 100° C. and do not form any mixed phases with water at temperatures in that range, and mixtures thereof;
   (B) 0.1 to 1% by weight of material selected from the group consisting of nonionic surface-active ethylene oxide adducts having an HLB value of 12–19.6, and mixtures thereof, as emulsifier; and
   (C) 39 to 74.9% by weight of water, said dispersion being flowable at 20° C.

2. An aqueous dispersion as claimed in claim 1, wherein component (A) is a $C_{14-22}$ fatty alcohol or a mixture of such fatty alcohols, a $C_{12-22}$ fatty acid or a mixture of such fatty acids, a fatty acid/ fatty alcohol ester of $C_{12-22}$ fatty acids and fatty alcohols, a $C_{16-44}$ dialkyl ether, an ethylene glycol or propylene glycol difatty acid ester or a fatty acid triglyceride of a $C_{12-18}$ fatty acid.

3. An aqueous dispersion as claimed in claim 2, wherein in the emulsifier is an adduct of 20 to 100 moles ethylene oxide with a $C_{12-22}$ fatty alcohol, with a $C_{12-22}$ fatty acid, with a fatty acid monoglyceride, a fatty acid sorbitan monoester or a fatty acid propylene glycol monoester of a $C_{12-22}$ fatty acid, with castor oil or hydrogenated castor oil, with an alkyl monoglycoside or oligoglycoside containing 12 to 22 carbon atoms in the alkyl group or with an alkylphenol containing 8 to 15 carbon atoms in the alkyl group.

4. An aqueous dispersion as claimed in claim 3, wherein the emulsifier is present in a quantity of 0.1 to 0.5% by weight, based on the dispersion as a whole.

5. An aqueous dispersion as claimed in claim 3, which contains a $C_{14-22}$ fatty alcohol in a quantity of 30 to 50% by weight as the fat and an adduct of 20 to 100 moles ethylene oxide with a $C_{16-22}$ fatty alcohol in a quantity of 0.1 to 0.5% by weight, based on the dispersion as a whole, as the emulsifier.

6. An aqueous dispersion as claimed in claim 4, which contains a $C_{14-22}$ fatty alcohol in a quantity of 30 to 50% by weight as the fat and an adduct of 20 to 100 moles ethylene oxide with a $C_{16-22}$ fatty alcohol in a quantity of 0.1 to 0.5% by weight, based on the dispersion as a whole, as the emulsifier.

7. An aqueous dispersion as claimed in claim 2, wherein the emulsifier is present in a quantity of 0.1 to 0.5% by weight, based on the dispersion as a whole.

8. An aqueous dispersion as claimed in claim 7, which contains a $C_{14-22}$ fatty alcohol in a quantity of 30 to 50% by weight as the fat and an adduct of 20 to 100 moles ethylene oxide with a $C_{16-22}$ fatty alcohol in a quantity of 0.1 to 0.5% by weight, based on the dispersion as a whole, as the emulsifier.

9. An aqueous dispersion as claimed in claim 2, which contains a $C_{14-22}$ fatty alcohol in a quantity of 30 to 50% by weight as the fat and an adduct of 20 to 100 moles ethylene oxide with a $C_{16-22}$ fatty alcohol in a quantity of 0.1 to 0.5% by weight, based on the dispersion as a whole, as the emulsifier.

10. An aqueous dispersion as claimed in claim 1, wherein the emulsifier is an adduct of 20 to 100 moles ethylene oxide with a $C_{12-22}$ fatty alcohol, with a $C_{12-22}$ fatty acid, with a fatty acid monoglyceride, a fatty acid sorbitan monoester or a fatty acid propylene glycol monoester of a $C_{12-22}$ fatty acid, with castor oil or hydrogenated castor oil, with an alkyl monoglycoside or oligoglycoside containing 12 to 22 carbon atoms in the alkyl group or with an alkylphenol containing 8 to 15 carbon atoms in the alkyl group.

11. An aqueous dispersion as claimed in claim 10, wherein the emulsifier is present in a quantity of 0.1 to 0.5% by weight, based on the dispersion as a whole.

12. An aqueous dispersion as claimed in claim 11, which contains a $C_{14-22}$ fatty alcohol in a quantity of 30 to 50% by weight as the fat and an adduct of 20 to 100 moles ethylene oxide with a $C_{16-22}$ fatty alcohol in a quantity of 0.1 to 0.5% by weight, based on the dispersion as a whole, as the emulsifier.

13. An aqueous dispersion as claimed in claim 10, which contains a $C_{14-22}$ fatty alcohol in a quantity of 30 to 50% by weight as the fat and an adduct of 20 to 100 moles ethylene oxide with a $C_{16-22}$ fatty alcohol in a quantity of 0.1 to 0.5% by weight, based on the dispersion as a whole, as the emulsifier.

14. An aqueous dispersion as claimed in claim 1, wherein the emulsifier is present in a quantity of 0.1 to 0.5% by weight, based on the dispersion as a whole.

15. An aqueous dispersion as claimed in claim 14, which contains a $C_{14-22}$ fatty alcohol in a quantity of 30 to 50% by weight as the fat and an adduct of 20 to 100 moles ethylene oxide with a $C_{16-22}$ fatty alcohol in a quantity of 0.1 to 0.5% by weight, based on the dispersion as a whole, as the emulsifier.

16. An aqueous dispersion as claimed in claim 1, which contains a $C_{14-22}$ fatty alcohol in a quantity of 30 to 50% by weight as the fat and an adduct of 20 to 100 moles ethylene oxide with a $C_{16-22}$ fatty alcohol in a quantity of 0.1 to 0.5% by weight, based on the dispersion as a whole, as the emulsifier.

* * * * *